United States Patent [19]
Farrell et al.

[11] Patent Number: 6,113,934
[45] Date of Patent: Sep. 5, 2000

[54] PLATINUM COMPLEXES WITH ANTI-VIRAL ACTIVITY AND METHOD OF USING SAME

[75] Inventors: Nicholas Farrell; Ulrich Bierbach, both of Richmond, Va.

[73] Assignee: Virginia Commonwealth University, Richmond, Va.

[21] Appl. No.: 09/095,565

[22] Filed: Jun. 11, 1998

[51] Int. Cl.$^7$ ............................. A01N 25/02; A61K 33/24
[52] U.S. Cl. ........................ 424/405; 424/649; 424/406; 514/492
[58] Field of Search ............................. 514/492; 424/649, 424/405, 406, 409, 418, 421, 420, 423

[56] References Cited

U.S. PATENT DOCUMENTS

| | | | |
|---|---|---|---|
| 4,053,587 | 10/1977 | Davidson et al. | 424/131 |
| 4,177,263 | 12/1979 | Rosenberg et al. | 424/131 |
| 5,093,134 | 3/1992 | Murrer et al. | 424/617 |
| 5,225,207 | 7/1993 | Barreau et al. | 424/649 |
| 5,275,827 | 1/1994 | Spinelli et al. | 424/649 |
| 5,562,925 | 10/1996 | Rosenberg et al. | 424/649 |
| 5,665,343 | 9/1997 | Sohn et al. | 424/78.26 |

FOREIGN PATENT DOCUMENTS 2755146   4/1998   France .

OTHER PUBLICATIONS

Neamati et al. Mol. Pharmacol. 52(6) 1041–1055, 1997.
Balcarova et al Mol Pharmacol 53(5) 846–855, 1998.
Coluccia et al Met.–Based Drugs 2(5) 249–56, 1995.
Hollis et al Cancer Res. 51(7) 1866–75, 1991.
Snyder et al J. Antimicrob. Chemother. 19(6) 815–22, 1987.
Hollis et al Mechanistic Studies of–Trisubstituted Platinum(II) Cancer Research 51 pp. 1866–1875, Apr. 1, 1991.
Balacarova et al DNA Interactions of a Novel Platinum Drug Molecular Pharmacology 53 pp. 846–855, 1998.
Neamati et al Potent Inhibitors Molecular Pharmacology 52 pp. 1041–1055, 1997.
Snyder et al J. Antimicrobial Chemotherapy 19 pp. 815–822, 1987.

*Primary Examiner*—Neil S. Levy
*Attorney, Agent, or Firm*—Whitham, Curtis & Whitham

[57] ABSTRACT

The present invention relates to treatment of viral infections, such as HIV, with a new class of anti-viral platinum coordination compounds having the general structural formula [PtXA$_m$B$_{3-m}$] where X is an anionic ligand, A is an acyclic, nitrogen containing monodentate ligand such as amines, ammines, and quinolines, and B is nucleobase.

17 Claims, 1 Drawing Sheet

PLATINUM COMPLEXES WITH ANTI-VIRAL ACTIVITY AND METHOD OF USING SAME

BACKGROUND OF THE INVENTION (1) Field of the Invention

The invention is generally related to platinum complexes having anti-viral activity and methods of using them for treating patients, including both humans and animals, with viral infections.

(2) Background Information

Platinum complex compounds have been proposed for use in pharmaceutical compositions for several types of medical treatments on animals.

For instance, U.S. Pat. No. 4,177,263 teaches the use of various platinum (II) and (IV) coordination compounds, such as chloroplatinumammines, for treatment of malignant tumors in animals. U.S. Pat. No. 5,562,925 is related to U.S. Pat. No. 4,177,263.

U.S. Pat. No. 5,225,207 teaches Pt complexes for pharmaceutical applications in treatment of cancers, in which amino-groups of a Pt(II) complex, e.g., a chloroplatinumammine derivative, form a part of the same heterocyclic ring including the Pt atom.

U.S. Pat. No. 5,275,827 teaches a platinum (II) complex useful as an anti-tumor agent in which the bidentate amine is retained in the formula while a heterocyclic sulphinyl carboxylate group is formed in lieu of the other two donor ligands and the heterocyclic ring includes the Pt atom as a ring atom.

U.S. Pat. No. 5,665,343 teaches an anticancer agent that is polymeric platinum (II) complex in which a bioactive diamineplatinum (II) moiety is incorporated into a polyphosphazene backbone of a polymer chain.

U.S. Pat. No. 4,053,587 teaches a method for treating animals afflicted with a viral infection with certain types of platinum coordination compounds of the formulae described therein. The preferred compounds are described as being cis-Pt(II)(NH$_3$)$_2$Cl$_2$ complexes, cis-Pt(IV)(NH$_3$)$_2$Cl$_4$ complexes, and cis-Pt(II)(H$_2$O)$_2$(NH$_3$)$_2$ complexes. The '587 patent also teaches certain trans-Pt(IV) compounds, as well as certain malonato platinum (II) and (IV) coordination compounds.

Although some advances have been made, there still remains a major need in the health field to develop and identify new compounds that have significant anti-HIV activity. As known, the HIV (human immunodeficiency virus), formerly referred to as HTLV-III, is a retrovirus that is the etiologic agent of AIDS (acquired immunodeficiency syndrome). As known, AIDS is a disease that compromises the competency of the immune system, characterized by persistent lymphadenopathy and various opportunistic infections, such as Pneumo-cystiscarnii pneumonia, cytomegalovirus, disseminated histoplasmosis, candidiasis, and isosporiasis, and so forth. In view of these pervasive effects on the body, the development of new drugs that will effectively treat an HIV-infected patient has been a challenging undertaking.

BRIEF SUMMARY OF THE INVENTION

The present invention satisfies the above and other objectives as it relates to effectively treating viral infections, such as HIV, with a new class of platinum compounds.

More particularly, the present invention relates to a method for preventing viral infections of a patient involving administering to the patient an effective anti-viral amount of a platinum coordination complex. The anti-HIV activity of platinum compounds of this invention has been experimentally established and confirmed by studies that are described in the examples herein.

DETAILED DESCRIPTION OF THE PREFERRED EMBODIMENTS OF THE INVENTION

Figure 1:
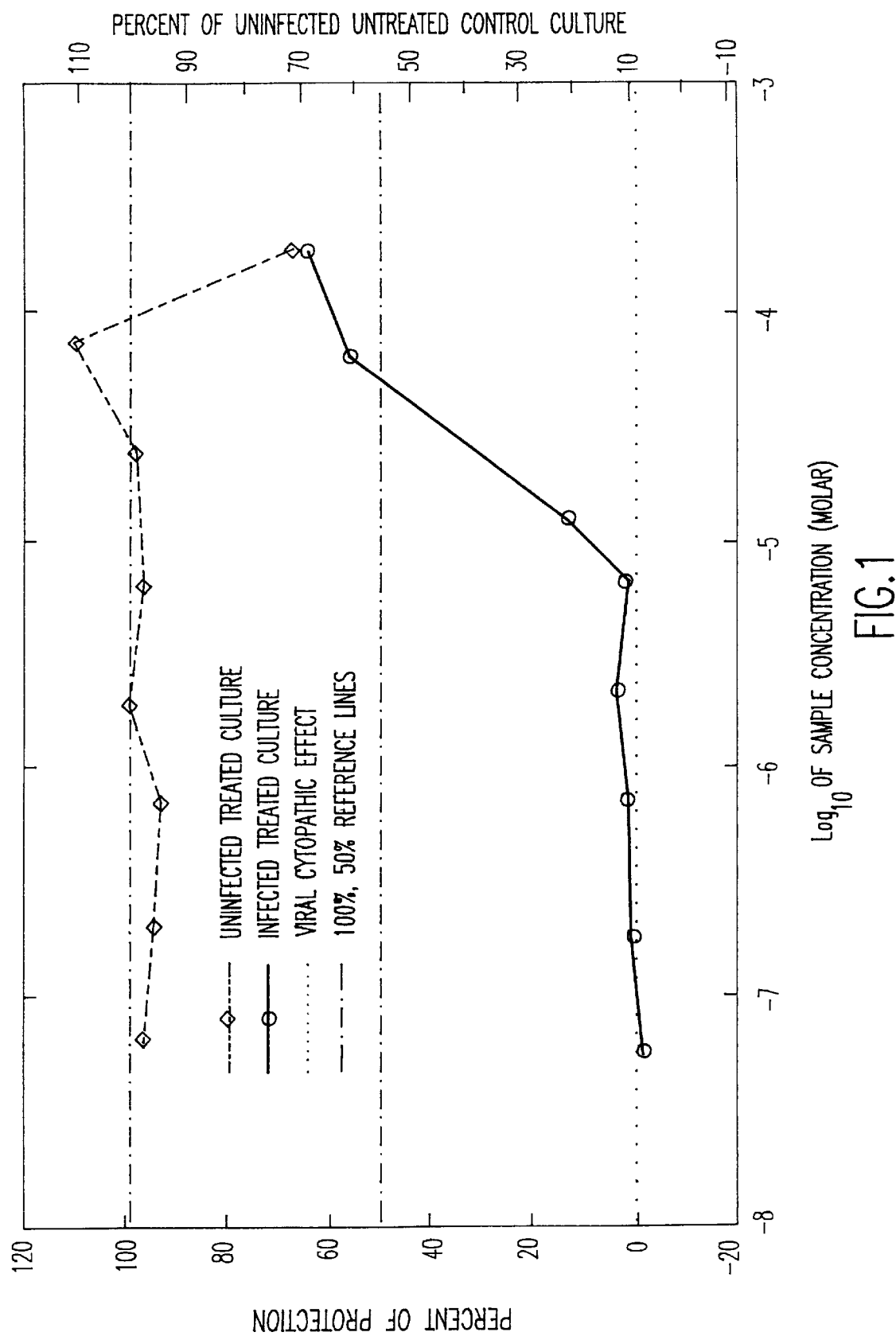
FIG. 1 is a graph showing the results of in vitro anti-HIV activity of a platinum complex of the invention.

The present invention relates to relieving and preventing viral infection in a host or patient. In particular, the method comprises administering to a host or patient an amount of a compound having the general structural formula:

X is an anionic ligand such as halogens (Cl, Br, I, or F), NO$_3$, ClO$_4$, hydroxyl, alkoxides and sulfhydryls, —OR and —SR respectively, where R is a hydrogen or alkyl moiety, and preferably a substituted or unsubstituted alkyl moiety (C$_{1-2}$ is preferred). Chloride is the preferred anionic ligand. A is an ammine (NH$_3$ linked directly to the platinum metal), a substituted or unsubstituted secondary or tertiary amine, or a substituted or unsubstituted heterocyclic amine, where the substituents are electrophilic or nucleophilic (e.g., C$_{1-12}$alkyl (—CH$_3$), —NO$_2$, —X (Cl, Br, I), —NR$_2$ (NMe$_2$)). The preferred heterocycles may include thiazole, benzothiazole, imidazole, isoquinoline, and quinoline; however other useful heterocycles may include oxazole, indole, and acridine. An example of a substituted heterocycle would include 4-Mepyridine. In the case where multiple A constituents are present, the constituents may be the same or different (e.g., all ammines or heterocyclic amines, etc.). B can be the same as A. For example, one compound within the family defined by the general structure noted above would be [PtCl(NH$_3$)$_3$]$^+$. However, it is preferred that B be a nitrogen containing nucleobase where the nitrogen is connected to the Pt moiety. Examples of nucleobases include purine and purine type compounds (guanine, adenine, hypoxanthine, xanthine, uric acid, caffeine, threobromine, etc.), pyrimidines (uracil, thymine, cytosine, methylcytosine, etc.) and pyrimidine derivatives (thiamine, etc.), nucleosides (guanosine, etc.), nucleotides (5'-guanosinemonophosphate, etc.), and oligonucleotide or defined polynucleotide sequences (e.g., an extension of deoxyribonucleic acid (DNA), ribonucleic acid (RNA) or peptidonucleic acids (PNA)). The preferred binding site of endocyclic nitrogens is N7 for purines and N3 for pyrimidines. Examples of compounds within the practice of this invention include trans[PtCl(9-ethylguanine-N7)(NH$_3$)$_2$] NO$_3$, and trans[PtCl(9-ethylguanine-N7)(NH$_3$)(quinoline)]. The structures of these compounds are set forth below as structures 1 and 2, respectively, and the synthesis and antiviral (particularly anti-HIV) activity is discussed in the Examples.

STRUCTURE ONE

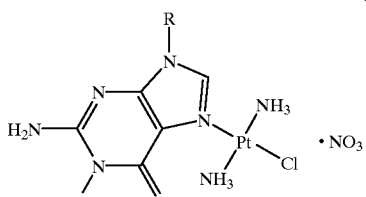

STRUCTURE TWO

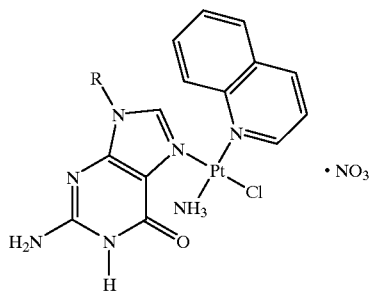

It should be noted that B is a monodentate, nitrogen containing, heterocyclic moiety in Structures one and two. In the case of nucleosides, nucleotides, and DNA, RNA, or PNA sequences, the Pt would be linked to the nitrogen of a nucleotide in the sequence in a manner similar to that shown above in the two chemical structures. Other exemplary structures which should be useful within the practice of this invention include trans-[PtCl(pyridine)$_2$(9-ethylguanine)]$^+$, trans-[PtCl(thiazole)$_2$(9-ethylguanine)]$^+$, and trans-[PtCl (NH$_3$)(pyridine)(9-ethylguanine)]$^+$.

Under the general structural formula noted above, there can be more than one B substituent, and, in these cases, the B substituents can be the same or different. In addition, under the general structural formula, m ranges between 0 and 3, whereby there may be as many as three A substituents or three B substituents connected to the Pt. Thus, it will be understood by those of skill in the art that compounds within this invention can have as many as three different N-containing heterocycles, or have as many as three identical N-containing heterocycles, as the B substituents. Platinum (II) forms dsp$^2$ complexes which are generally planar. The geometry of [PtXA$_m$B$_{3-m}$] may either by cis or trans for X related to B. As is shown in the two above-identified structures, the preferred embodiment has the anionic ligand trans to the nucleobase (e.g., Cl trans to 9-Ethylguanine).

The platinum compounds of the formula of the present invention, each of which has at least one ligand thereof formed of heterocyclic ring including N as a ring member, can be synthetically derived from a haloplatinumammine starting compound. Haloplatinumammine compounds, such as cis or trans-Pt(II)(NH$_3$)$_2$Cl$_2$, can be synthesized by well known methods, such as described in the textbook references listed at col. 3, lines 45–59 of U.S. Pat. No. 4,053,587, which teachings are incorporated by reference. In any event, the haloplatinumammine compound, such as cis or trans-Pt (II)(NH$_3$)$_2$Cl$_2$, is dissolved in an organic solvent, such as an aprotic solvent of dimethylformamide (DMF) or dimethyl-sulfoxide (DMSO), and then reacting the haloplatinumammine compound with AgNO$_3$ to precipitate AgCl. After filtering off the AgCl, the filtrate will be mixed with a heterocyclic compound including a nitrogen in a ring member thereof which will form a Pt-ligand bond assuming the position of the Cl atom eliminated from the complex in the previous reaction step, and the mixture is permitted to react over an extended period time with stirring. The solvent (e.g., DMF) is then removed by volatizing it to yield a crystalline product.

To provide a platinum compound of this invention having a second ligand constituted by a heterocyclic compound including a nitrogen in a ring member thereof, it is merely necessary to repeat the above reaction scheme on the Pt complex reaction product derived from the first run through the synthesis procedure except, in the second run, introducing the second heterocyclic compound desired for the second ligand in the reaction step of precipitating AgCl. It is understood that in providing a Pt complex with two ligands that are heterocyclic groups including a N atom in the ring in this manner, that the starting haloplatinumammine compound will need to have two halo groups available for the overall reaction.

While a cis or trans-Pt(II)(NH$_3$)$_2$Cl$_2$ compound has no charge, it is understood that other chloroplatinumammine compounds also could be used as a starting material in the above reaction scheme, even if they bear a charge. For example, trichloroamineplatinate (II) has a (−) charge while chlorotriamineplatinum (II) has a (+) charge. These chloroplatinumamine compounds exist in the solid state as salts in conjunction with appropriate oppositely charged ions, e.g., positively charged Pt complexes are generally prepared as nitrates or halides while negatively charged Pt complexes are generally prepared as ammonium or alkali metal salts.

Likewise, it should be understood that the compounds of the present invention [PtXA$_m$B$_{3-m}$], which are administered to a patient for antiviral applications, particularly including anti-HIV treatment, can be charged or uncharged. For example, the molecule PtCl(NH$_3$)$_3$$^+$ has a positive charge.

Charged compounds can be put in the form of salts by association with oppositely charged ions. For example, structures one and two above are associated with nitrate ions. As discussed above in conjunction with the starting materials, the Pt complexes of this invention can take the form of solid state salts where the positively charged Pt complexes will generally take the form of nitrates or halides while negatively charged Pt complexes are generally prepared as ammonium or alkali metal salts.

The platinum complexes used in the Examples reported herein were prepared, and purified by crystallization and stored in the dark until needed for testing. Test solutions were freshly prepared immediately prior to use by dissolving the test complex in physiological saline.

The pharmaceutical compositions of the present invention including the platinum coordination complex compounds described herein can be used with suitable pharmaceutically acceptable carriers. Where the composition is adapted for parenteral administration, the platinum coordination compounds may be dissolved or suspended in a suitable carrier liquid such as physiological saline, buffered saline, distilled water, and so forth. It will be understood that where the pharmaceutical compositions contemplated by this invention are intended for intravenous administration that the platinum compounds will be introduced in solution form. Where the platinum compounds described herein are intended for intramuscular or subcutaneous administration, they can be administered in either solution or suspension form.

Many other modes of administration may also be employed for the platinum compounds of this invention, and these will necessitate the use of different carriers, adjuvants, elixirs, and the like. For example, the compounds can be suspended in chlorofluorocarbon or hydrofluorocarbon propellants for delivery via inhaler to the lungs. Alternatively, the platinum compounds could be formulated in a matrix (lactose, etc.) or carrier (e.g., liposomes, etc.) which will allow delivery orally, sublingually or by suppository.

The administration of pharmaceutical compositions of the present invention can be intermittent, or at a gradual, or continuous, constant or controlled rate to a patient (human or animal). In addition, the time of day and the number of times per day that the pharmaceutical formulation is administered can vary. The host or patient for the therapeutic treatment using the platinum compounds described herein generally are mammalian, such as humans, dogs, and rodents, and so forth. The effective dose can vary depending upon factors such as the mode of delivery; sex, age, and other conditions of the patient; and the severity of the viral infection.

Generally, for parenteral administration in humans, dosages in the range of from about 0.1 to about 500 mg active Pt compound/kg body weight/24 hr., more preferably 1.0 to 10.0 mg active Pt compound/kg body weight/24 hr., for a patient afflicted with the viral infection is generally effective. The level of efficacy and optimal amount of dosage for any given platinum complex of this invention can vary one from the other depending on the virus being treated.

The pharmaceutical compositions including the platinum complex agents of this invention also can include pharmaceutically acceptable additives or adjuncts to the extent that they do not hinder or interfere with the therapeutic effect desired of the Pt complex anti-viral agent. Examples of these could include preservatives (e.g., benzalkonium chloride, methyl paraben, etc.); colorants; surfactants (TWEEN, oleic acid, etc.); and binders or encapsulants (lactose, liposomes, etc.).

In the following examples, objects and advantages of this invention are further illustrated by various embodiments thereof but the details of those examples should not be construed to unduly limit this invention.

All parts and percentages in the examples are by weight unless otherwise indicated.

EXAMPLES

Example 1

Trans[PtCl(9-ethylguanine-N7)($NH_3$)$_2$]$NO_3$, structure one above, was synthesized in the following manner.

To a solution of 1 mmol of trans-[$PtCl_2(NH_3)_2$] in 25 ml of anhydrous DMF was added 0.170 g (1 mmol) of $AgNO_3$. After stirring this mixture at room temperature for 16 hours, the precipitated AgCl was filtered off through a celite pad. To the filtrate was added 0.179 g (1 mmol) of 9-ethylguanine, and the mixture was allowed to stir for 12 hours. The DMF was removed under reduced pressure at 30° C. After addition of 50 mL of diethyl ether, the remaining oil solidified. The obtained crude product was recrystallized from methanol to give 0.380 g (white needles, yield 75%). The trans[PtCl(9-ethylguanine-N7)($NH_3$)$_2$]$NO_3$ product was confirmed by NMR spectroscopy and elemental analysis.

Example 2

Trans[PtCl(9-ethylguanine-N7)($NH_3$)(quinoline)]$NO_3$, structure two above, was synthesized in the following manner.

A starting material, trans-[$PtCl_2(NH_3)$(quinoline)] was prepared according to the method of Van Beusichem et al., *Inorg. Chem.*, 1992, 31, 634. To a solution of 1 mmol of trans-[$PtCl_2(NH_3)$(quinoline)] in 25 ml of anhydrous DMF was added 0.170 g (1 mmol) of $AgNO_3$. After stirring this mixture at room temperature for 48 hours, the precipitated AgCl was filtered off through a celite pad. To the filtrate was added 0.179 g (1 mmol) of 9-ethylguanine, and the mixture was allowed to stir for 30 hours. The DMF was removed under reduced pressure at 30° C. After addition of 50 mL of diethyl ether, the remaining oil solidified. The obtained crude product was recrystallized from methanol to give 0.410 g (white needles, yield 66%). The trans[PtCl(9-ethylguanine-N7)($NH_3$)(quinoline)]$NO_3$ product was confirmed by NMR spectroscopy and elemental analysis.

Example 3

Studies were performed to investigate the anti-HIV effects of the platinum complex compound made in Example 2 above. More specifically, the anti-viral activity of this compoun dwas evaluated in vitro for the HIV virus according to the standard protocols established by the National Cancer Institute for prospective anti-HIV agents. A separate nontreated culture was used as a control for these investigations.

The procedure used in the National Cancer Institute's test for agents active against human immunodeficiency virus is designed to detect agents acting at any stage of the virus reproductive cycle. The assay basically involves the killing of T4 lymphocytes by HIV. Small amounts of HIV are added to cells, and two cycles of virus reproduction are necessary to obtain the required cell killing. Agents that interact with virions, cells, or virus gene products to interfere with viral activities will protect cells from cytolysis. All tests compared with at least on positive (e.g., AZT-treated) control done at the same time under identical conditions. The procedure used herein is outlined below:

1. Candidate agent (i.e., platinum complex of this invention) is dissolved in DMSO then diluted 1:100 in cell culture medium before preparing serial half-log dilutions. T4 lymphocytes (CEM cell line) are added and after a brief interval HIV-1 is added, resulting in a 1:200 final dilution of the compound. Uninfected cells with the compound serve as a toxicity control, and infected and uninfected cells without the compound server as basic controls.

2. Cultures are incubated at 37° C. in a 5% carbon dioxide atmosphere for six days.

3. The tetrazolium salt, XTT, is added to all wells, and cultures are incubated to allow formazan color development by viable cells.

4. Individual wells are analyzed spectrophotometrically to quantitate formazan production, and, in addition, are viewed microscopically for detection of viable cells and confirmation of protective activity.

5. Drug-treated virus-infected cells are compared with drug-treated non-infected cells and with other appropriate controls (untreated infected and untreated non-infected cells, drug containing wells without cells, etc.) on the same plate.

The results are set forth in Table 1 below for the compound of structure two, and they are also graphically shown in FIG. 1.

TABLE 1

| Dose (molar) | Percent of Protection | Percent of Control | |
|---|---|---|---|
| | | Infected | Uninfected |
| $6.35 \times 10^{-8}$ | −1.68 | 5.44 | 97.25 |
| $2.00 \times 10^{-7}$ | 0.63 | 7.59 | 96.10 |
| $6.34 \times 10^{-7}$ | 1.71 | 8.59 | 94.39 |
| $2.00 \times 10^{-6}$ | 3.10 | 9.88 | 100.11 |
| $6.33 \times 10^{-6}$ | 0.73 | 7.68 | 96.29 |
| $2.00 \times 10^{-5}$ | 12.74 | 18.85 | 98.11 |
| $6.32 \times 10^{-5}$ | 58.91 | 61.79 | 107.84 |
| $2.00 \times 10^{-4}$ | 69.28 | 71.43 | 75.11 |

It is apparent from the results that the presence of the platinum coordination compound provided a significant level of protection of the cells against infection by HIV. These results are also suggestive that the platinum compounds of the present invention will be effective against many other types of viral infectants (e.g., influenza, hepatitis, papilloma, etc.).

While the invention has been described in terms of its preferred embodiments, those skilled in the art will recognize that the invention can be practiced with modification within the spirit and scope of the appended claims.

We claim:

1. A method for treating a patient afflicted with a viral infection, comprising administering to said patient an effective anti-viral amount of a platinum coordination compound of the formula $$[PtXA_mB_{3-m}]$$

where m ranges from 0 to 2,
where X is an anionic ligand directly bonded to platinum,
where A is a substituent selected from the group consisting of $NH_3$, substituted or unsubstituted secondary and tertiary amines and substituted or unsubstituted heterocyclic amines where the substituents are electrophilic or nucleophilic, and in the case of more than one A moiety the moieties may be the same or different, and
where B is a heterocyclic nucleobase with a nitrogen in a ring which is connected to Pt, and in the case of more than one B moiety the moieties may be the same or different,
and wherein if two of said A substituents are present and are both $NH_3$ the configuration of said two $NH_3$ A substituents is trans with respect to Pt.

2. The method of claim 1 wherein said viral infection is human immunodeficiency virus.

3. The method of claim 1 wherein said effective antiviral amount ranges from about 0.1 mg/kg body weight/24 hr/patient to about 500 mg/kg body weight/24 hr/patient.

4. The method of claim 1 wherein said step of administration is performed by parenteral administration.

5. The method of claim 1 wherein X is trans to B.

6. The method of claim 1 wherein X is selected from the group consisting of halogens, $NO_3$, $ClO_4$, hydroxyls, alkoxides, and sulfhydryls.

7. The method of claim 6 wherein X is chloride.

8. The method of claim 1 wherein B is a heterocyclic nucleobase selected from the group consisting of purines and pyrimidines, nucleosides, nucleotides, oligonucleotides and polynucleotides.

9. The method of claim 1 wherein said platinum coordination compound is selected from the group consisting of trans[PtCl(9-ethylguanine-N7)($NH_3$)$_2$]$NO_3$, and trans[PtCl(9-ethylguanine-N7)($NH_3$)(quinoline)]$NO_3$.

10. The method of claim 1 wherein said B is a heterocyclic amine.

11. The method of claim 10 wherein said heterocyclic amine is selected from the group consisting of substituted and unsubstituted thiazoles, benzothiazoles, imidazoles, isoquinolines, quinolines, oxazole, indoles, and acridines.

12. A platinum coordination compound with the formula, $$[PtXA_mB_{3-m}]$$

where m ranges from 0 to 2,
where X is an anionic ligand directly bonded to platinum,
where A is a substituent selected from the group consisting of $NH_3$, substituted or unsubstituted secondary and tertiary amines and substituted or unsubstituted heterocyclic amines where the substituents are electrophilic or nucleophilic, and in the case of more than one A moiety the moieties may be the same or different, and
where B is a heterocyclic nucleobase with a nitrogen in a ring which is connected to Pt, and in the case of more than one B moiety the moieties may be the same or different,
and wherein if two of said A substituents are present and are both $NH_3$ the configuration of said two $NH_3$ A substituents is trans with respect to Pt.

13. The platinum coordination compound of claim 12 wherein B is a heterocyclic nucleobase selected from the group consisting of purines and pyrimidines, nucleosides, nucleotides, oligonucleotides and polynucleotides.

14. The platinum coordination compound of claim 12 wherein X is selected from the group consisting of halogens, $NO_3$, $ClO_4$, hydroxyls, alkoxides and sulfhydryls.

15. The platinum coordination compound of claim 12 selected from the group consisting of trans[PtCl(9-ethylguanine-N7)($NH_3$)$_2$]$NO_3$, and trans[PtCl(9-ethylguanine-N7)($NH_3$)(quinoline)]$NO_3$.

16. The platinum coordination compound of claim 12 wherein said B is a heterocyclic amine.

17. The platinum coordination compound of claim 16 wherein said heterocyclic amine is selected from the group consisting of substituted and un substituted thiazoles, benzothiazoles, imidazoles, isoquinolines, oxazole, indoles, and acridines.

* * * * *